United States Patent [19]
Stewart et al.

[11] Patent Number: 5,994,148
[45] Date of Patent: Nov. 30, 1999

[54] METHOD OF PREDICTING AND ENHANCING SUCCESS OF IVF/ET PREGNANCY

[75] Inventors: Dennis R. Stewart, Sacramento; Catherine A. Vandervoort, El Macero, both of Calif.

[73] Assignee: The Regents of University of California, Oakland, Calif.

[21] Appl. No.: 08/879,662

[22] Filed: Jun. 23, 1997

[51] Int. Cl.$^6$ .............................. G01N 33/53; C07K 14/64
[52] U.S. Cl. ........................... 436/510; 436/501; 436/65; 530/399; 530/412; 435/7.92
[58] Field of Search .................................. 530/300, 399, 530/398, 412; 514/2, 8, 12; 436/510, 501, 65; 435/7.92

[56] References Cited

U.S. PATENT DOCUMENTS

| | | |
|---|---|---|
| 3,845,770 | 11/1974 | Theeuwes et al. . |
| 3,995,651 | 12/1976 | Adams . |
| 4,034,756 | 7/1977 | Higuchi et al. . |
| 4,111,202 | 9/1978 | Theeuwes . |
| 4,320,759 | 3/1982 | Theeuwes . |
| 4,449,983 | 5/1984 | Cortese et al. . |
| 4,835,251 | 5/1989 | Burnier et al. . |
| 5,023,088 | 6/1991 | Wong et al. . |
| 5,166,191 | 11/1992 | Cronin et al. . |
| 5,451,572 | 9/1995 | Cipolla et al. . |

FOREIGN PATENT DOCUMENTS

| | | |
|---|---|---|
| WO 94/09805 | 5/1994 | WIPO . |
| WO 94/21815 | 9/1994 | WIPO . |
| WO 97/30175 | 8/1997 | WIPO . |

OTHER PUBLICATIONS

Stewart et al., "Relaxin secretion by human granulosa cell culture is predicative of IVF–ET pregnancy success." *Thirtieth Annual Meeting of the Society for the Study of Reproduction*, Portland Oregon, U.S.A. Aug. 2–5, 1997, *Biology Reproduction* 56 (Suppl. 1) 1997.

Eddie et al., "Relaxin in Sera During the Luteal Phase on In Vitro Fertilization Cycles." *Br J Obstet Gynaecol* 97(3):215–220 (1990).

Bell et al., "Relaxin Levels in Antenatal Patients Following In Vitro Fertilizationn" *Fertil Steril* 52(1):85–87 (1989).

Bell et al., "Levels of Relaxin in In Vitro Fertilization Pregnancies in the First Trimester Measured with a Homologous Radioimmunoassay for Human Relaxin." *Fourth World Conference on In Vitro Fertilization*, Melbourne, Australia, Nov. 18–22, 1985, *J. In Vitro Fert Embryo Transfer* 3(3):184 (1986).

Arthur et al. Human Reproduction 11(1): 88–91, 1996.

Gagliardi et al. Fertil. Sterilit. 58(2): 314–320, 1992.

Bell et al. Fertil. Steril. 52(1): 85–87, 1989.

Norma et al. Fertil. Steril. 59(1): 130–137, 1993.

Br. J. Obstet. & Gynecol. Eddie et al. 97: 215–220, 1990.

Lee, Anne, et al., "Shark Cartilage Contains Inhibitors of Tumor Angiogenesis" *Science* (1983) 221:1185–1187.

Moses, Marsha A., et al., "Identification of an Inhibitor of Neovascularization from Cartilage" *Science* (1990), pp. 1408–1410.

Stewart, Dennis R., et al., "Relaxin in the Peri–Implantation Period" *Clinical Endocrinology and Metabolism* (1990) 70(6):1771–1773.

Stewart, Dennis R., et al., "The Relationship Between hCG and Relaxin Secretion in Normal Pregnancies vs Peri–Implantation Spontaneous Abortions" *Clinical Endocrinology* (1993) 38:379–385.

Stewart, Dennis R., et al., "Enhanced Ovarian Steroid Secretion before Implantation in Early Human Pregnancy" *J. Clinical Endocrinology and Metabolism* (1993) 76(6):1470–1476.

*Primary Examiner*—Michael P. Woodward
*Attorney, Agent, or Firm*—Karl Bozicevic; Bozicevic, Field & Francis LLP

[57] ABSTRACT

A method of determining the probability of an in vitro fertilization (IVF) or embryo transfer (ET) method being successful is disclosed. Relaxin can be measured directly in the serum or indirectly by culturing granulosa lutein cells extracted from the patient as part of an IVF/ET procedure. A method of enhancing the rate of a successful pregnancy resulting from an IVF/ET procedure is also disclosed whereby relaxin is administered.

7 Claims, 3 Drawing Sheets

METHOD OF PREDICTING AND ENHANCING SUCCESS OF IVF/ET PREGNANCY

STATEMENT AS TO FEDERALLY SPONSORED RESEARCH

Material described in this application was supported in part by NIEHS PO1ES06198, RR 00169, and grant No. 5 P42 ES04699 from the National Institute of Enviromental Health Sciences, NIH with funding provided by EPA. The Government may have certain rights in this invention.

FIELD OF THE INVENTION

The invention relates generally to the field of assays and methods of treatment. In particular the invention relates to determining relaxin levels and relating the levels to the probability of success in an in vitro fertilization or embryo transfer procedure.

BACKGROUND OF THE INVENTION

Reproductive failure is a serious problem that has been addressed clinically by in vitro fertilization (IVF) and embryo transfer (ET). These procedures might be expected to yield exceptionally high conception rates as in vitro fertilization provides an already fertilized ova for transfer into a fully primed recipient. Despite these efforts the success rate of IVF/ET is less than ideal. In the published data for IVF/ET in the United States and Canada in 1994, there were 26,961 initiated cycles of standard IVF. Of these, 86.2% led to a retrieval and of these 90.2% led to a transfer. However, the overall success rate in terms of clinical pregnancies was 22.7% per initiated cycle and a 29.1% pregnancy rate per transfer. Additionally, there appears to be a high incidence of early pregnancy loss after in vitro fertilization with a biochemical pregnancy rate of 18% and a spontaneous abortion rate of 27%. Thus, it appears that the IVF technique has been well optimized but implantation failure may be the cause for a large number of losses with ET and this implantational loss is an area of potential improvement.

The factors which contribute to the success of in vitro fertilization/embryo transfer (IVF/ET) have been extensively studied. In looking at what factors may affect implantation, many studies have reported correlations of hormonal or measurement of other parameters with conception rate. High conception rates have been associated with lowered follicular phase PP14 concentrations, large increases in PP14 concentrations from the day of hCG stimulation to the day of embryo transfer, high preretrieval concentrations of CA-125, large increases in CA-125 from the day of hCG stimulation to oocyte retrieval, increased uterine blood flow, increased uterine artery impedance, and an inhibition of uterine motility in the periimplantation period. It has also been suggested that lowered estradiol concentrations at the time of ovulation induction lowered progesterone concentrations at the time of hCG stimulation, or the magnitude of the increase in progesterone in response to hCG stimulation have a higher success of conception. These reports generally fail to determine the mechanism by which these observations are translated into impaired conception.

Few studies have examined the relationship between granulosa lutein cell culture and the characteristics of the cycle from which cells were obtained. One group found that decreased granulosa cell 11 beta hydroxysteroid dehydrogenase activity was associated with higher conception rates. It was reasoned that exposure of the oocyte to cortisol was necessary for proper functional maturation and high amounts of enzyme in the cumulus cells could prevent this exposure. Another study was based upon observations that the magnitude of rise in progesterone concentrations in response to hCG stimulation was correlated with implantation success. They found that patients with an increase of 3 fold in response to hCG were more likely to get pregnant (46%) than those with a P4 increase of less than 3 fold who had only a 14% conception rate. Granulosa lutein cell culture from these patients showed differences in hormone production. Patients with a large serum P4 increase had higher progesterone concentrations in culture. Patients with a low P4 increase had more variable estrogen concentrations in culture but the estrogen was more responsive to gonadotropin stimulation.

SUMMARY OF THE INVENTION

A method of predicting the probability of a successsful pregnancy resulting from in vitro fertilization (IVF) or embryo transfer (ET) based on relaxin levels is disclosed. The relaxin levels may be determined by culturing granulosa lutein cells (preferably for ten days) extracted from the patient as part of the IVF/ET procedures. A method of enhancing the rate of successful term pregnancy is provided by administering relaxin in amounts sufficient to raise relaxin levels.

An object of the invention is to provide a method of determining the probability of obtaining successful in vitro fertilization or embryo transfer.

Another object is to determine relaxin concentration of cultured granulosa lutein cells at about days after extraction and relating the level to a standard to determine the probability of a successful IVF/ET procedure.

Another object is to determine relaxin levels in serum and relate the level directly to IVF/ET success probability or indirectly by first relating such to relaxin levels of cultured granulosa lutein cells.

Another object of the invention is to provide a method for determining the success rate for IVF/ET procedures by assaying for levels of glycodelin, specifically glycodelin released from the endometrium.

Yet another object of the invention is to measure levels of hCG and relate the levels to a standard which relates to relaxin levels thereby determining the probability of success with IVF/ET procedures.

Yet another object of the invention is to provide a method for predicting the success of an IVF/ET procedure by measuring levels of relaxin, glycodelin, hCG in any combination and relating those levels to a standard.

Yet another object of the invention is to provide a method for enhancing the success rate of an IVF/ET procedure by administering into a patient any of relaxin, glycodelin or hCG.

Another object is to provide a method and formulation for enhancing the success rate for IVF/ET procedures.

An advantage is that measured relaxin levels are predictive of success rates for conception and for obtaining a term pregnancy.

An advantage of the invention is that the assay is highly predictive of resulting in a successful pregnancy when relaxin levels are at 800 pg/ml or more.

A feature of the invention is that it requires measurement of only a single hormone.

DEFINITIONS

Figure 1:
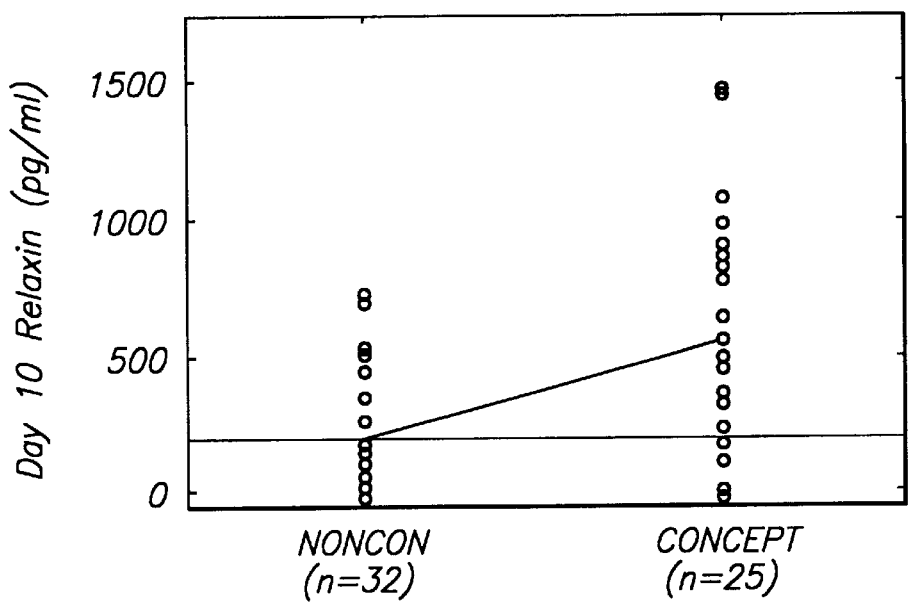
FIG. 1 is a graph showing relaxin concentration on day 10 of cultured granulosa cells from 57 human female patients grouped based on whether conception occurred where n is the number of patients and the line connects the mean value in each group.

The term "relaxin" refers to mature human relaxin which is a hormone peptide of approximately 6,000 daltons which can be made by processes described in U.S. Pat. No. 4,835,251 and (PCT US94/0699). Methods of using relaxin in cardiovascular therapy and in the treatment of neurodegenerative diseases are described in U.S. Pat. No. 5,166,191 and in (PCT US92/06927). Certain formulations of human relaxin are described in U.S. Pat. No. 5,451,572, issued Sep. 19, 1995.

The terms "conception", "conceptive" and the like as used herein refers to detecting hCG in serum after a IVF/ET procedure and nonconceptive refers to the absence of hCG in serum after the hCG used to stimulate ovulation clears from the blood.

The term "successful IVF/ET procedure" means conception resulted from a IVF/ET procedure and preferably went to term.

"Optional" or "optionally" means that the subsequently described event or circumstance may or may not occur, and that the description includes instances where said event or circumstance occurs and instances in which it does not.

The term "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particular a human, and includes:

(a) preventing the disease or symptom such as infertility from occurring in a subject which may be predisposed to the disease or symptom but has not yet been diagnosed as having it;

(b) inhibiting the disease symptom (e.g., infertility), i.e., arresting its development; or (c) relieving the disease symptom, i.e., causing regression of the disease or symptom (successful pregnancy).

The term "effective amount" means a dosage sufficient to provide treatment for the disease state being treated, e.g., infertility. This will vary depending on the patient, the disease, e.g., the type of infertility and the treatment being effected. In the ase of pregnancy, an "effective amount" is that amount necesary to substantially improve the likelihood of successful pregnancy, in particular that amount which improves the likelihood of successfully completing the first trimester, and especially of successfully causing the embryo to implant. An effective amount should be sufficient to achieve a successful result in at least 65% of the pregnancies tested, more preferably in at least 75%, still more preferably at least 85%, and most preferably should provide for a successful implantation in at least 95% of the occassions administered, in the absence of other complicating factors. The dosage administered may be adjusted based on the level of relaxin measured in the particular patient being treated.

The terms "standard", "standard level", "standardized relaxin level" and the like are used interchangeably herein to define a determined concentration of relaxin obtained from taking a number of readings—preferably a statistically significant number of readings. The standard can be arbitrarily fixed depending on the level of success a reading above or below the standard is to indicate. Based on present data a culture level at day 10 above 800 pg/ml would appear to indicate a 100% chance of success. The percentage would be expected to decrease when larger numbers of patients are tested.

DETAILED DESCRIPTION OF PREFERRED EMBODIMENTS

Before the present assays and methods are disclosed and described, it is to be understood that this invention is not limited to particular assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

The present invention includes a cell culture system for human luteinizing granulosa cells which supports the timely and dynamic secretion of estrogen (E2), progestrone (P4) and relaxin in patterns that mimic serum patterns of secretion of these hormones during the luteal phase of the menstrual cycle. The results obtained provide a profile of relaxin secretion similar to that of a normal nonconceptive menstrual cycle. The results also show that the amount of relaxin produced from cells taken from different human female patients is highly variable. Relaxin production on day 10 of culture ranged from 1500 pg/ml to undetectable in cultures from different patients. Those patients showing a relaxin level above 800 pg/ml showed 100% success rate and those showing levels below 200 pg/ml showed a 6.7% success rate.

Figure 3:
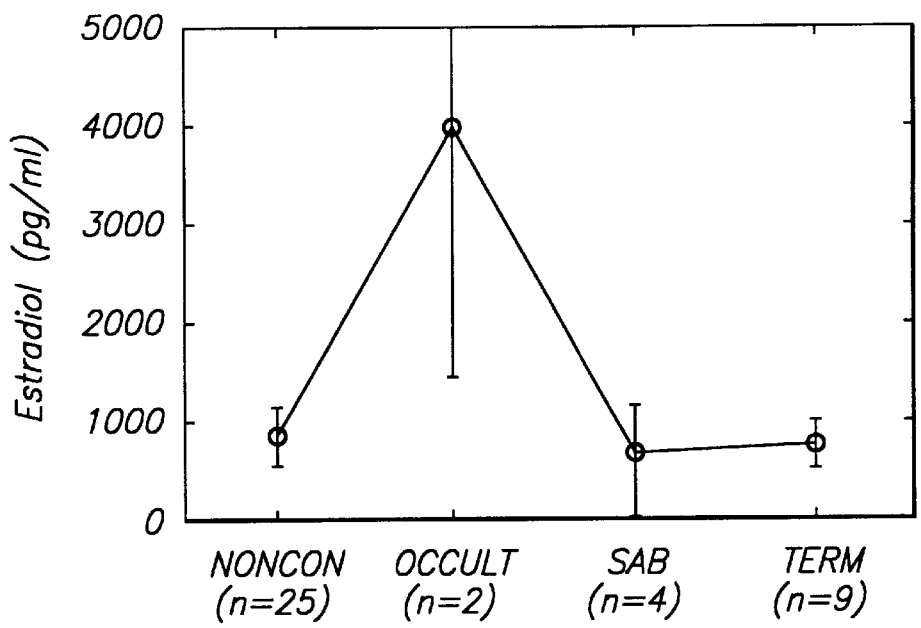
FIG. 3 is a graph showing the mean estadiol concentration of all patients in the group on day 10 of cultured granulosa cells with the patients grouped by: no conception (NONCON); occult-pregnancy ended soon (OCCULT); spontaneous abortion (SAB); and term deliveries (TERM).
Figure 4:
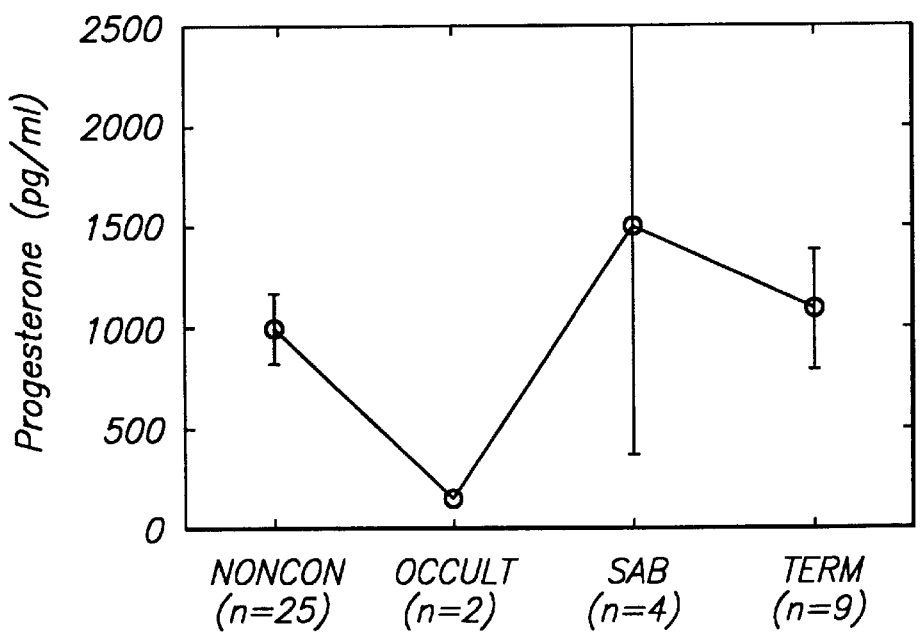
FIG. 4 is a graph showing the mean progesterone concentration of all patients in the group on day 10 of cultured granulosa cells with the patients grouped by: no conception (NONCON); occult-pregnancy ended soon (OCCULT); spontaneous abortion (SAB); and term deliveries (TERM).
Figure 5:
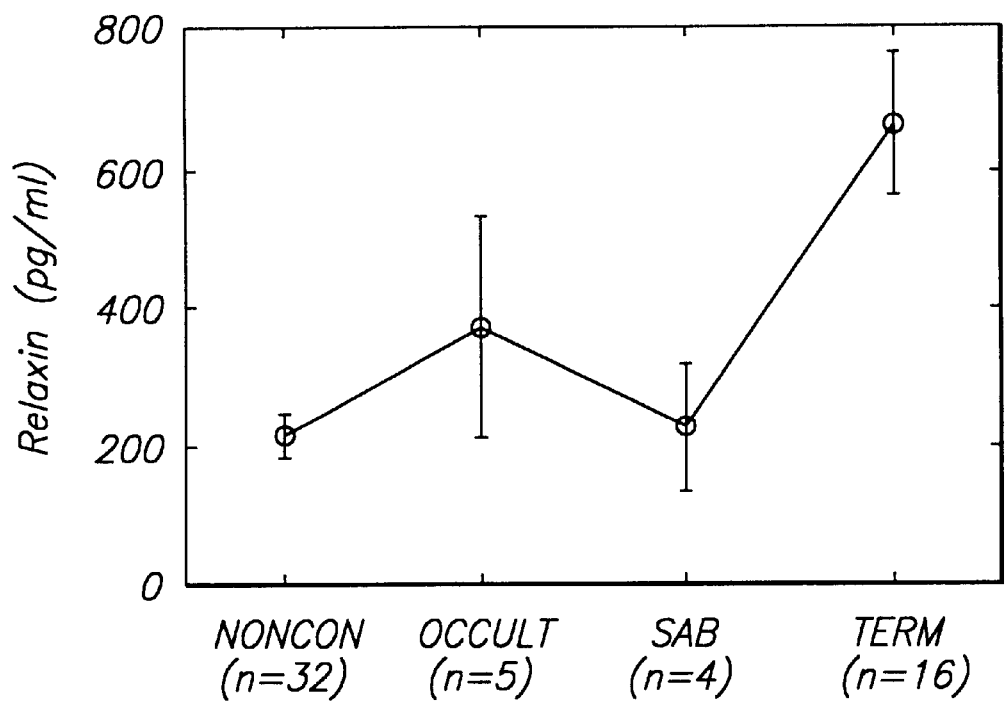
FIG. 5 is a graph showing the mean relaxin concentration of all patients in the group on day 10 of cultured granulosa cells with the patients grouped by: no conception NONCON); occult-pregnancy ended soon (OCCULT); spontaneous abortion (SAB); and term deliveries (TERM).

The magnitude of relaxin secretion during the middle of granulosa lutein cell culture is significantly correlated with pregnancy success while steroid production is not (see FIGS. 3, 4 and 5). This shows that relaxin is involved in the normal implantation process and that lowered relaxin concentrations result in poor IVF/ET pregnancy rates.

In examining the endocrine responses from granulosa lutein cells in culture, it was noted that there was an excellent correlation of relaxin concentrations during the middle of the culture period (day 10) and the detection of conception in the cycle from which the cells were obtained. Few cycles with low relaxin from the cell culture showed signs of implantation or had a successful pregnancy while cycles with high relaxin had a high rate of conception.

Table 1 is divided arbitrarily into two sections with the first showing relaxin levels below 200 pg/ml with thirty patients and the second portion showing relaxin levels above 200 pg/ml with twenty-seven patients.

TABLE I

| Subject | Age | GLCC Relaxin | Pregnancy |
|---|---|---|---|
| 1 |  | −23 | − |
| 2 | 36 | −22 | + |
| 3 | 28 | −21 | + |
| 4 | 38 | −14 | − |
| 5 | 40 | −13 | − |
| 6 | 29 | −9 | − |
| 7 | 31 | −6 | − |
| 8 |  | −4 | + |
| 9 | 37 | 0 | − |
| 10 | 28 | 3 | + |
| 11 | 37 | 18 | − |
| 12 | 36 | 19 | − |
| 13 | 36 | 37 | − |
| 14 | 34 | 48 | − |
| 15 | 41 | 68 | − |
| 16 | 37 | 111 | + |
| 17 | 34 | 111 | − |
| 18 | 33 | 112 | − |
| 19 | 30 | 146 | − |
| 20 | 39 | 149 | − |
| 21 | 34 | 151 | − |
| 22 | 39 | 155 | − |
| 23 | 39 | 159 | − |
| 24 | 38 | 159 | − |
| 25 | 34 | 164 | − |
| 26 | 39 | 174 | + |
| 27 | 35 | 179 | − |
| 28 | 31 | 184 | + |
| 29 | 37 | 191 | − |
| 30 |  | 196 | − |
| MEAN | 35.2 | 80.9 | 23− 7+ |
| Relaxin above 200 pg/ml | | | |
| 31 | 38 | 235 | + |
| 32 | 32 | 273 | − |
| 33 | 38 | 324 | + |
| 34 | 33 | 328 | + |
| 35 |  | 358 | − |
| 36 | 37 | 365 | + |
| 37 |  | 457 | − |
| 38 | 36 | 464 | + |

TABLE I-continued

| Subject | Age | GLCC Relaxin | Pregnancy |
|---|---|---|---|
| 39 | 34 | 496 | + |
| 40 | 37 | 517 | − |
| 41 | 30 | 526 | − |
| 42 | 37 | 544 | − |
| 43 | 35 | 558 | + |
| 44 | 30 | 637 | + |
| 45 | 37 | 700 | − |
| 46 | 34 | 723 | − |
| 47 | 26 | 736 | − |
| 48 | 32 | 768 | + |
| 49 | 32 | 781 | + |
| 50 | 39 | 823 | + |
| 51 | 32 | 857 | + |
| 52 | 39 | 898 | + |
| 53 | 27 | 905 | + |
| 54 |  | 983 | + |
| 55 |  | 1075 | + |
| 56 | 44 | 1453 | + |
| 57 |  | 1470 | + |
| MEAN | 34.5 | 676.5 | 9− 18+ |

The results shown in Table I are summarized below in Table II showing that 18 of 27 patients (66.7%) in the higher relaxin level group conceived whereas only 7 of the 30 (23.3%) patients in the lower relaxin level group conceived.

TABLE II

| Relaxin | NonConceptive | Conceptive |
|---|---|---|
| >200 pg/ml | 9 | 18 |
| <=200 pg/ml | 23 | 7 |

The results are even more dramatic when focusing on all cycles with granulosa lutein cell production of relaxin >800 pg/ml (14% of the cycles had relaxin concentrations in this range) had term pregnancies. Conversely, only 3.5% of cycles with relaxin <200 pg/ml (53% of all cycles had relaxin in this range) had term pregnancies.

TABLE III

| Relaxin (pg/ml) | NonConceptive | Conceptive |
|---|---|---|
| >800 | 0 | 8 |
| 200–800 | 9 | 10 |
| <200 | 23 | 7 |

Tables IV and V show that the results are even more dramatic when considering success rates based not just on obtaining conceptions but on obtaining a term pregnancy.

TABLE IV

| (Same Groups as Table II above) | | |
|---|---|---|
| Relaxin | Non-Term | Term |
| >200 pg/ml | 13 | 14 |
| <=200 pg/ml | 28 | 2 |

TABLE V (Same Groups as Table III above)

| Relaxin (pg/ml) | Non-Term | Term |
|---|---|---|
| >800 | 0 | 8 |
| 200–800 | 13 | 6 |
| <200 | 28 | 2 |

Levels of relaxin can be measured by extracting granulosa cells from the patient along with an in vitro fertilization procedure. The granulosa cells can be cultured in the manner specifically described within Example 58. Cellular extract can be removed each day and relaxin levels or levels of other hormones measured each day with the measured liquid then being discarded. In general, relaxin begins to appear around day 6 or 7 and maximizes at around day 10. Accordingly, it is most desirable to determine the relaxin level at day 10. Similar procedures can be used for the measurement of hormones such as glycodelin or hCG. Further, any of these hormones can be measured in blood serum.

Steroid concentrations of estadiol and progesterone from cultured cells were not predictive of conception. While it has generally been accepted that estrogen and progesterone are sufficient to adequately prepare the endometrium, it is noted that endometrial morphology does not always imply normal endometrial receptivity. The ability of some pregnancies to survive with estradiol and progesterone treatment alone (such as in premature ovarian failure patients) does not preclude other hormonal adjuvants from improving the conception rate in IVF. As the embryo transfer success rate is poor, there may be additional ovarian factors which would optimize conception rates. The data provided here show that additional relaxin improves implantation and pregnancy success rates in IVF/ET.

THEORY OF RELAXIN EFFECT

Without being bound to any particular theory of how or why relaxin might effect a successful pregnancy it is pointed out that there are several means by which lowered circulating relaxin concentrations might influence implantation success. Perhaps the most profound and least studied actions of relaxin on endometrial development may be on the vasculature. Hypertrophy and hyperplasia of endothelium in maternal blood vessels of the uterine endometrium during gestation in monkeys occur in the first month of pregnancy. This reaction can be induced and enhanced in nonpregnant and castrated monkeys by giving estrogen, progesterone and relaxin in proper sequence. Relaxin induces dilation of superficial endometrium blood vessels and proliferation of the endothelial cells. The effects produced seem to be a direct response of the endothelium to relaxin, as they occur only when this hormone is administered.

During the follicular phase in women, spiral arteries have a straight course but in the secretory phase they grow longer, thicker and become spirally twisted. On the 9th day after ovulation, groups of spiral arterioles become prominent. This is closely timed to the increase in relaxin that we have observed in circulation during the luteal phase where relaxin is first detected about day 6–7 and then rapidly increases. Thus luteal endometrial blood vessel development and angiogenesis may be important to the implantation process and success of the pregnancy.

Angiogenesis has been shown to have an essential role in implantation as demonstrated by administration to pregnant mice of an agent which inhibits angiogenesis. Treatment with AGM1470 O-chloracetyl carbamoyl fumagillol prior to or shortly after implantation prevented all live births while administration at midpregnancy had no effect on fetal survival. Uterine artery blood flow measured on the day of oocyte retrieval as measured by Doppler flow measurements was positively correlated with pregnancy success in IVF. It has also been demonstrated that in women with impaired uterine perfusion the administration of low dose aspirin is associated with improved blood flow and improved pregnancy rates. Spiral artery development is also known to be important for proper implantation as the invasive cytotrophoblast shows preference for maternal vessels in early implantation. Inadequate invasion and remodeling has been associated with pregnancies complicated by hypertension and intrauterine growth retardation and has been suggested as a cause of miscarriages. Deficient invasion of trophoblast cells into the endometrium and failure of the remodeling of the uterine spiral arteries are histopathological hallmarks of preeclampsia.

Another possible mechanism by which relaxin could be involved in aiding a successful implantation is through the stimulation of glycodelin release by the endometrium. Relaxin is a direct stimulus for glycodelin secretion. Glycodelin is a potent immunosuppressive which may be needed to prevent maternal rejection of the embryo. For this reason measuring levels of glycodelin should provide a predictor of IVF/ET success.

Relaxin is highly effective in reducing the amplitude of spontaneous and induced uterine contractions in several species. Endometrial wavelike movement occurs during menstrual cycle and cycles with few waves have a greater conception rate. However, porcine relaxin and synthetic human relaxin have little or only a slight effect on spontaneous contractility of human myometrial tissue. Thus, relaxin may play a minor role in uterine quiescence in the human although it remains to be determined if administered relaxin will cause uterine quiesce in vitro.

DOSAGE AND ADMINISTRATION

Relaxin is administered at a therapeutically effective dosage, e.g., a dosage sufficient to treat infertility and improve the chance of successful term pregnancy.

Administration of relaxin can be via any of the accepted modes of administration for agents that serve similar utilities, preferably by systemic administration.

While human dosage levels for treating infertility have yet to be optimized for relaxin, generally, a daily dose is from about 0.1 to 500.0 µg/kg of body weight per day, preferably about 6.0 to 200.0 µg/kg, and most preferably about 12.0 to 100.0 µg/kg. Generally it is sought to obtain a serum concentration of relaxin approximating or greater than normal circulating levels in pregnancy, i.e., 1.0 ng/ml, such as 0.5 to 50 ng/ml, preferably 1.0 to 20 ng/ml. For administration to a 70 kg person, the dosage range would be about 7.0 µg to 3.5 mg per day, preferably about 42.0 µg to 2.1 mg per day, and most preferably about 84.0 to 700.0 µg per day. The amount of relaxin administered will, of course, be dependent on the subject and the severity of the affliction, the manner and schedule of administration and the judgment of the prescribing physician.

In employing relaxin for treatment of infertility, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bio-erodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages. The compositions will typically include a conventional pharmaceutical carrier or excipient and relaxin. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of relaxin, the remainder being suitable pharmaceutical excipients, carriers, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The formulations of human relaxin described in U.S. Pat. No. 5,451,572, issued Sep. 19, 1995, incorporated herein by reference, are particularly preferred.

Parenteral administration is generally characterized by injection, either subcutaneously, intradermally, intramuscularly or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably the composition will comprise 0.2–2% of the relaxin in solution.

A more recently devised approach for parenteral administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of relaxin in the present invention.

EXAMPLES

The following examples are put forth so as to provide those of ordinary skill in the art with a complete disclosure and description of how to make and use the assays and methods of the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Examples 1–57

Fifty-seven human female patients ranging in age of from 26 to 44 (age not determined in eight patients) were assayed to determine the level of relaxin. Granulosa cells (GCs) were extracted from each patient as part of IVF/ET procedures. When the amount of relaxin produced by granulosa lutein cell cultures (n=57) was grouped by cycle outcome, either nonconceptive or conceptive, it was found that the mean for nonconceptives was lower than for conceptives (FIG. 1). The methods and materials used in the Examples are described in a separate section below and the details of the assay produced are provided in Example 58.

The results for the 57 patients were divided into those less than or equal to 200 pg/ml on day 10 of culture as shown in Table II. The cultures could also be divided into three groups: <–200 pg/ml, and >800 pg/ml as shown in Table III. This also resulted in a significant association of relaxin and conception success.

Figure 2:
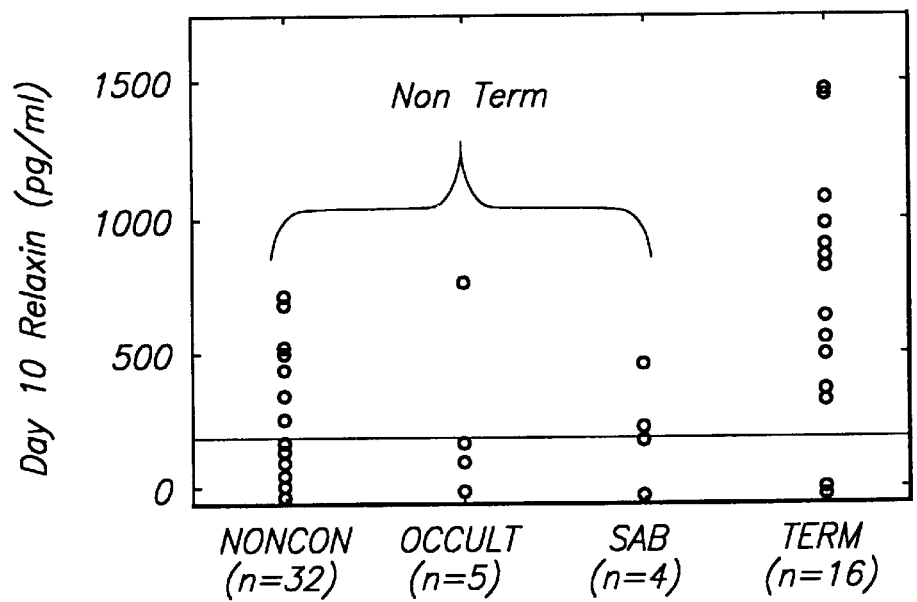
FIG. 2 is a graph showing relaxin concentration on day 10 of cultured granulosa cells with the patients grouped by: no conception (NONCON); occult-pregnancy ended soon (OCCULT); spontaneous abortion (SAB); and term deliveries (TERM).

The conceptive cycles could be subdivided into occults (short term gestation) spontaneous abortions (SABs after longer term pregnancies), and termgestations (FIG. 2). This data could be tabled into term pregnancies and non-term cycles which consisted of nonceptive cycles, occults and SABs (Table IV). There was a positive association of relaxin concentrations with term pregnancy. Using the criteria of three levels of relaxin secretion also resulted in a positive association of relaxin concentrations and a successful gestation (Table V).

A comparison of mean levels of estradiol or progesterone did not show a significant difference between levels from nonconceptive cycles vs term cycles (FIGS. 3 and 4). Relaxin was the only hormone of the three measured that showed a significant difference between nonconceptive and conceptive cycles (FIGS. 3, 4 and 5). More specifically, the estrogen (E2) and progesterone (P4) levels of the granulosa cells were also measured and shown to not be directly related to a likelihood of a successful and/or unsuccessful pregnancy.

Details for the methods and materials used to obtain these results are provided below.

MATERIALS AND METHODS

Culture Conditions

Culture conditions were those described in Stewart, et al., J. Clin. Endo. Metabol (1997). Briefly, extracellular matrix was applied to culture dishes on the same day cells were collected according to the manufacturer's directions. Minimal Essential Medium (MEM, Gibco, Grand Island, N.Y.) is modified with the following additions: sodium bicarbonate, 4.4 mg/100 ml MEM (Sigma), fungizone, 1 ml/100 ml (Gibco); penicillin G, 6 mg/100 ml (Sigma); streptomycin sulfate, 6 mg/100 ml (Sigma) and 10% fetal calf serum (Hyclone, Logan, Utah). Media is filtered through a 0.22 micron sterile syringe filter (Fisher, Santa Clara, Calif.) and equilibrated at 37 C and 5% $CO_2$ in air prior to use. HCG (Pregnyl, Organon, W. Orange, N.J.) was added to the culture media in amounts as described below.

Cell Collection

Human granulosa cells (GCs) were obtained by ultrasound-guided follicle aspiration from women receiving assisted reproduction treatment at Pacific Fertility Center (Sacramento, Calif.). The cells were a by-product of the IVF/ET procedure and are normally discarded. They were provided as coded samples with the identities of the women unavailable.

The patients received varying doses of Metrodin (Serono) and Progonal (Serono) and received 10,000 IU of hCG 36 hrs prior to folicular aspiration. Approximately 1.0 ml modified human Tubal Fluid Media (Irvine Scientific, Santa Ana, Calif.) containing HEPES buffer, antibiotics, and heparin, was added to the follicular fluid during the oocyte retrieval procedure. After oocytes and cumulus masses were removed, the follicular fluid containing granulosa cells was refrigerated and transported on ice to California Regional Primate Research Center in a 50 ml flask. Individual follicles were not distinguished as all granulosa cells from an individual were pooled. Cells from different subjects were not pooled.

Assays

Estradiol and progesterone were measured by commercial kits (Diagnostics Products Corp., Los Angeles, Calif.) as described in Stewart, et al., J. Clin. Endo. Metab. 76:1470–1476 (1993). Relaxin was measured by an enzyme immunoassay as in the manner which serum relaxin was measured in Stewart, et al., J. Clin. Endo. Metab. 7-:1771–3 (1990). The assay was modified by dilution of human relaxin using culture fluid instead of human serum for preparation of standards.

Data Analysis

To normalize the endocrine data, the values were converted to the common logarithm for statistical analysis and averaging. Data were converted to arithmetic scale for graphing (geometric mean).

Example 58

Correlation of Relaxin Cconcentration and IVF/ET Success

Media and Plate Preparation

Minimal Essential Medium (MEM, Gibco, Grand Island, N.Y.) is modified with the following additions: sodium bicarbonate, 4.4 mg/100 ml MEM (Sigma); fungizone, 1 ml/100 ml (Gibco); penicillin G, 6 mg/100 ml (Sigma); streptomycin sulfate, 6 mg/100 ml (Sigma) and 10% fetal calf serum (Hyclone, Logan, Utah). Media is filtered through a 0.22 micron sterile syringe filter (Fisher, Santa Clara, Calif.) and equilibrated at 37° C. and 5% $CO_2$ in air prior to use. HCG (Pregnyl, Organon, W. Orange, N.J.) was added to the culture media in amounts as described below.

Extracellular matrix was applied to culture dishes according to the manufacturer's directions on the same day cells were collected. A thin layer (50 µl/well) of Matrigel (Collaborative Biomedical, Bedford, Mass.) is applied to the bottom of 4 well plates (Nunc) with a 100 µl pipette tip and rapidly spreading the Matrigel with the tip. All plates, matrigel and pipets are kept on ice during the coating procedure. Coated plates are incubated at 37° C. for 30 min. in 5% $CO_2$ to set the Matrigel and were then ready for use.

Cell Collection

Human granulosa cells (GCs) were obtained by ultrasound-guided follicle aspiration from women receiving assisted reproduction treatment. Approximately 1.0 ml modified human Tubal Fluid Media (Irvine Scientific, Santa Ana, Calif.) containing HEPES buffer, antibiotics, and heparin, was added to the follicular fluid aspirate during the oocyte retrieval procedure. After oocytes and cumulus masses were removed, the follicular fluid containing granulosa cells was refrigerated and transported on ice to California Regional Primate Research Center in a 50 ml flask.

Culture Preparation

All cell preparation was performed under a laminar flow hood to maintain sterile conditions. Follicular fluid was divided equally into 15 ml disposable, sterile centrifuge tubes and centrifuged at 300×g for 5 min and then at 500×g for an additional 5 min. This created a firm layer of GCs on top of a red blood cell pellet. The layer of GCs were collected from each tube with a Pasteur pipette and combined in a sterile 15 ml centrifuge tube. About 4 ml MEM was added and the GCs were gently aspirated through a 1.0 ml disposable pipet tip to break up clumps. One ml aliquots of this cell suspension were layered onto 1.0 ml 40% Percoll (Sigma, St. Louis, Mo.) in PBS columns in 15 ml centrifuge tubes and centrifuged at 500×g for 30 min. The GC layer was removed from each Percoll column and combined in a sterile 15 ml centrifuge tube. Cells were washed twice with 5–10 ml fresh MEM and centrifuged for 10 min. at 300×g. The supernatant was discarded and the pellet was resuspended in 2–4 ml of MEM (commercial/minimum essential medium eagle). GCs were filtered through an 89 micron polyester filter (Spectra/Mesh) just prior to being counted and plated.

Cells were counted on a hemacytometer and brought to a final concentration of $1 \times 10^5$ cells/ml in MEM and plated on 4 well plates (1.9 cm diameter wells) at $5 \times 10^4$ cells/well. Cells had attached after 24 hrs and media was changed to remove remaining debris. Media was changed daily in all experiments and stored frozen until assay for hormone concentrations.

HCG Protocol

A baseline concentration of 0.02 IU/ml was selected based upon its ability to provide good steroid and relaxin secretion. HCG concentrations were held at baseline hCG for each of the 20 days of culture. Media is changed daily.

Verification of Viability and Cell Number During Culture

Cells were prepared, plated and cultured as described above with multiple wells for each patient. Estimates of viability were obtained using trypan blue (0.4%, Gibco) exclusion on an Olympus CK2 microscope at 200×. On the day cell number was to be verified, media was removed from the well and cells were rinsed 3 times with cold PBS (Sigma). One ml of Matrisperse (Fisher) was added to each well to free cells from the Matrigel and cells were scraped into a centrifuge tube. The well was rinsed with an additional 1 ml of Matrisperse which was placed in the tube and kept on ice for 1 hour.

Cells were centrifuged for 5 min at 500×g and pellet was resuspended in 100 mM PBS. Cells were counted on a hemacytometer.

Assays

Estradiol and progesterone were measured by commercial kits (Diagnostic Products Corp., Los Angeles, Calif.). Relaxin was measured by an enzyme immunoassay as previously reported for serum relaxin. The assay was modified by dilution of human relaxin using culture fluid instead of human serum for preparation of standards.

Data Analysis

Relaxin concentrations at day 10 of culture were used to determine if the cells are responders or nonresponders. Values of less than or equal to 200 pg/ml are considered nonresonders while relaxin concentrations >200 pg/ml are considered to be responders. If the relaxin concentrations are greater than 200 pg/ml the chances are that a successful pregnancy will result—noting that the probability of success increases to about 100% at relaxin concentration at or above 800 pg/ml. If relaxin concentrations are less than 200 pg/ml it indicates that either there will not be a conception or that the pregnancy will not continue to term.

It is possible that as more patients are examined, the current cutoff point of 200 pg/ml of relaxin on day of culture will be modified. It is possible the a different concentration of relaxin will be more predictive. It is also possible that days other than day of culture could be useful. Relaxin secretion begins about day 5 of culture and it is probable that differences would be significant by day 7 or 8 of culture if appropriate cutoff concentrations of relaxin are determined.

Examples 59 and 60

Two human female patients underwent IVF and extracted granulosa cells were cultured as in Example 58 above. Both patients showed no detectable level of relaxin at day 10. Serum extracted from the patients over the same time also showed a corresponding level of relaxin. Neither patient conceived. These examples show a relationship between serum relaxin levels and levels in the cell culture per the present invention. This shows that low relaxin production in cell culture corresponds to abnormally low relaxin in circulation and that this lack is not compensated for by feedback mechanisms. This is also consistent with low circulating relaxin being a cause of failure to conceive or pregnancy loss.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A method of determining a probability of success with an in vitro fertilization or embryo transfer procedure, comprising:
   determining a relaxin level in a patient;
   comparing the determined level to a standard level; and
   determining the probability of success based on the comparison;
   wherein the relaxin level is determined from a level produced by cultured granulosa cells obtained from the patient.

2. The method of claim 1, wherein the relaxin level is measured after culturing the granulosa cells for at least about seven days after removal from the patient.

3. The method of claim 2, wherein the relaxin level is measured on about the tenth day of culturing after removal from the patient.

4. The method of claim 3, wherein the relaxin level is determined by culturing granulosa cells are cultured in minimum essential medium eagle.

5. The method of claim 1, further comprising:
   determining a glycodelin level in the patient;
   determining an hCG level in the patient; and
   comparing the glycodelin and hCG levels to a standard; and
   determining the probability of success based on a combination of the comparisons for each of relaxin, glycodelin and hCG.

6. A method of determining a probability of success with an in vitro fertilization or embryo transfer procedure, comprising:
   extracting a sample from a patient wherein the sample comprises oocyte cells and granulosa cells;
   fertilizing an extracted oocyte cell;
   implanting the fertilized oocyte in the patient;
   culturing the extracted granulosa cells;
   measuring a level of relaxin produced by the cultured cells;
   comparing the measured relaxin level to a standard level; and
   determining the probability of success of in vitro fertilization or embryo transfer procedure based on the comparison.

7. The method of claim 6, wherein the level of relaxin is measured on about the tenth day of culturing.

* * * * *

UNITED STATES PATENT AND TRADEMARK OFFICE
CERTIFICATE OF CORRECTION

PATENT NO: 5,994,148
DATED: November 30, 1999
INVENTOR(S): Dennis R. Stewart et al.

It is certified that error appears in the above-identified patent and that said Letters Patent are hereby corrected as shown below:

Please correct the spelling of the second inventor's name from "Catherine A. Vandervoort" to --Catherine A. VandeVoort--.

Signed and Sealed this

Twenty-fourth Day of April, 2001

*Attest:*

NICHOLAS P. GODICI

*Attesting Officer*  *Acting Director of the United States Patent and Trademark Office*